US006123819A

United States Patent [19]
Peeters

[11] Patent Number: 6,123,819
[45] Date of Patent: Sep. 26, 2000

[54] NANOELECTRODE ARRAYS

[75] Inventor: John P. Peeters, Bethesda, Md.

[73] Assignee: Protiveris, Inc., Bethesda, Md.

[21] Appl. No.: 09/044,350

[22] Filed: Mar. 19, 1998

Related U.S. Application Data

[60] Provisional application No. 60/065,373, Nov. 12, 1997.

[51] Int. Cl.$^7$ .................................................. G01N 27/26
[52] U.S. Cl. ............................................ 204/403; 204/412
[58] Field of Search ........................... 204/403, 400, 204/412, 280; 435/287.1; 422/68.1

[56]        References Cited

U.S. PATENT DOCUMENTS

| | | |
|---|---|---|
| H201 | 1/1987 | Yager . |
| 4,452,682 | 6/1984 | Takata et al. . |
| 4,568,444 | 2/1986 | Nakamura et al. . |
| 4,777,019 | 10/1988 | Dandekar . |
| 4,908,112 | 3/1990 | Pace . |
| 4,981,572 | 1/1991 | Eastmunt et al. . |
| 4,983,510 | 1/1991 | Lardinois et al. . |
| 5,019,238 | 5/1991 | Cormier et al. . |
| 5,156,810 | 10/1992 | Ribi . |
| 5,192,507 | 3/1993 | Taylor et al. . |
| 5,281,539 | 1/1994 | Schramm . |
| 5,310,469 | 5/1994 | Cunningham et al. . |
| 5,328,847 | 7/1994 | Case et al. . |
| 5,332,479 | 7/1994 | Uenoyama et al. . |
| 5,384,028 | 1/1995 | Ito . |
| 5,395,587 | 3/1995 | Brigham-Burke et al. . |
| 5,409,583 | 4/1995 | Yoshioka et al. . |
| 5,494,831 | 2/1996 | Kindler . |
| 5,532,128 | 7/1996 | Eggers et al. . |
| 5,567,301 | 10/1996 | Stetter et al. . |
| 5,582,697 | 12/1996 | Ikeda et al. . |
| 5,607,567 | 3/1997 | Yun et al. . |
| 5,624,537 | 4/1997 | Turner et al. . |
| 5,730,940 | 3/1998 | Nakagawa ............................... 422/68.1 |
| 5,795,782 | 8/1997 | Church et al. ................................ 436/2 |
| 5,910,286 | 6/1999 | Lipsker ................................... 422/68.1 |

FOREIGN PATENT DOCUMENTS 02276966  11/1990  Japan .

OTHER PUBLICATIONS

CAPLUS abstract of Clowes et al. ("Improved methods for structural studies of proteins using nuclear magnetic resonance spectrotroscopy", Curr. opin. Biotechnol. (1995, 6(1), 81–8).
P. 45 of "Principles of Biological Chemistry" by David Page, Willard Grant Press, 1976.
JAPIO abstract of Hajme et al. (JP 02276966), Nov. 1990.
CAPLUS abstract of Costa–Kramer et al. ("Metallic nanowires: conductance statistics, stability, IV curves, and magnetism", NATO ASI Set., Ser. E (1997), 340 (nanowires), 171–190).
D.M. Kolb, R. Ullmann, T. Will, "*Nanofabrication of Small Copper Clusters on Gold (111) Electrodes by a Scanning Tunneling Microscope*". Science Magazine, vol. 275, Feb. 21, 1997, pp. 1097–1099.
Leo Kouwenhoven, "*Single–Molecule Transistors*". Science Magazine, vol. 275, Mar. 28, 1997, pp. 1897–1898.
Science, Jun. 11, 1999, vol. 284, p. 1754, article entitled "From the Bioweapons Trenches, New Tools for Battling Microbes".

*Primary Examiner*—Jill Warden
*Assistant Examiner*—Alex Noguerda
*Attorney, Agent, or Firm*—Dykema Gossett PLLC

[57]         ABSTRACT

An array of electrodes at the atomic or nano scale (nanoelectrodes) is built on a chip. The spatial distribution, height, width and electrochemical composition of the nanoelectrodes is varied, such that protein-specific electronic receptors are built directly on the chip with the nanoelectrodes without the use of any specific binding agents or molecules. Because of their size, a very large number of different receptors can be built as arrays on a single chip. The chip can be used to detect, characterize and quantify single molecules in solution such as individual proteins, complex protein mixtures, DNA or other molecules.

28 Claims, 3 Drawing Sheets

NANOELECTRODE ARRAYS

This application claims the benefit of U.S. Provisional Application Ser. No. 60/065,373 filed Nov. 12, 1997.

TECHNOLOGICAL FIELD

The present invention relates generally to methods and apparatus for detecting and characterizing single biological molecules in solution and, more specifically, to detect and characterize individual proteins, protein mixtures, DNA or other molecules on a chip.

BACKGROUND OF THE INVENTION

The characterization and quantification of individual proteins or complex biological molecules is extremely important in fields as distant as medicine, forensics and the military. For example in medicine the presence and concentration of given proteins can be used for disease or pre-disease diagnoses. In the military given proteins can be used to signal the presence or absence of given pathogens in the environment which is extremely important for example in potential germ warfare situations.

The detection of individual proteins or molecules in biological samples is currently complex and generally requires sophisticated and bulky equipment.

Several technologies have recently been disclosed to characterize given biological molecules. In particular success has been achieved in high density DNA chips build by Affymetrix as originally described in PCT International Publication No. WO 90/15070.

U.S. Pat. No. 5,624,537, entitled "BIOSENSOR AND INTERFACE MEMBRANE", describes a protein-receiving matrix and a single electrode.

U.S. Pat. No. 5,395,587, entitled "SURFACE PLASMON RESONANCE DETECTOR HAVING COLLECTOR FOR ELUTED LIGATE", describes a system to measure immobilized ligands using a plasmon resonance detector.

U.S. Pat. No. 5,607,567 entitled "PROTAMINE-RESPONSIVE POLYMERIC MEMBRANE ELECTRODE", describes a membrane electrode.

U.S. Pat. No. 5,328,847 entitled "THIN MEMBRANE SENSOR WITH BIOCHEMICAL SWITCH", describes a biosensor with a specific recognition biomolecule.

U.S. Pat. No. 4,777,019 entitled "BIOSENSOR", describes a biosensor for biological monomers.

U.S. Pat. No. 5,532,128, entitled "MULTI-SITE DETECTION APPARATUS", describes test wells combined with electrodes to detect given biological molecules.

U.S. Pat. No. 4,983,510 entitled "ENZYMES IMMOBILIZED ON LATEX POLYMER PARTICLES FOR USE WITH AN AMINO ACID ELECTROSENSOR", describes an electrosensor with a latex polymer trap.

U.S. Pat. No. 5,384,028 entitled "BIOSENSOR WITH A DATA MEMORY", describes a membrane biosensor with a memory module.

U.S. Pat. No. 5,567,301 entitled "ANTIBODY COVALENTLY BOUND FILM IMMUNOBIOSENSOR", describes an antibody biosensor.

U.S. Pat. No. 5,310,469 entitled "BIOSENSOR WITH A MEMBRANE CONTAINING BIOLOGICALLY ACTIVE MATERIAL", describe s a membrane biosensor.

U.S. Pat. No. 5,019,238 entitled "MEANS FOR QUANTITATIVE DETERMINATION OF ANALYTE IN LIQUIDS", describes a means to sequentially test the ionic concentration of fluids.

U.S. Pat. No. 4,981,572 entitled "ELECTRODE UNIT AND PACKAGE FOR A BLOOD ANALYZER", describes an electrode and apparatus to analyze blood.

U.S. Pat. No. 4,452,682 entitled "APPARATUS FOR MEASURING CLINICAL EMERGENCY CHECK ITEMS OF BLOOD", describes an apparatus to measure multiple elements in blood.

U.S. Pat. No. 4,568,444 entitled "CHEMICAL SUBSTANCE MEASURING APPARATUS", describes an electrode to quantify chemical substances in a solution.

U.S. Pat. No. 5,281,539 entitled "IMMUNOASSAY DEVICE FOR CONTINUOUS MONITORING", describes a two step immunoassay device.

U.S. Pat. No. 5,192,507 entitled "RECEPTOR-BASED BIOSENSORS", describes a biosensor based on a polymeric film to detect opiates.

U.S. Pat. No. 5,156,810 entitled "BIOSENSORS EMPLOYING ELECTRICAL, OPTICAL AND MECHANICAL SIGNALS", describes a thin layer biosensor.

U.S. Pat. No. 5,494,831 entitled "ELECTROCHEMICAL IMMUNOSENSOR SYSTEM AND METHODS", describes an immunologic biosensor.

U.S. Pat. No. 5,332,479 entitled "BIOSENSOR AND METHOD OF QUANTITATIVE ANALYSIS USING THE SAME", describes an electrode based sensor with a biologically active receptor.

U.S. Pat. No. 5,582,697 entitled "BIOSENSOR, AND A METHOD AND A DEVICE FOR QUANTIFYING A SUBSTRATE IN A SAMPLE LIQUID USING THE SAME", describes a biosensor based on the measure of reduction between a substrate and an oxidoreductase.

U.S. Pat. No. 4,908,112 entitled "SILICON SEMICONDUCTOR WAFER FOR ANALYZING MICRONIC BIOLOGICAL SAMPLES", describes a micro capillary separation device with detector capabilities.

U.S. Pat. No. 5,409,583 entitled "METHOD FOR MEASURING CONCENTRATIONS OF SUBSTRATES IN A SAMPLE LIQUID BY USING A BIOSENSOR", describes a two step biosensor.

U.S. Statutory Invention H201 entitled "BIOSENSORS FROM MEMBRANE PROTEINS RECONSTITUTED IN POLYMERIZED LIPID BILAYERS", describes a method for incorporating and using cell membrane proteins in biosensors.

The above described technologies are generally used for the detection of a single type or a few different types of molecules. None of these technologies are particularly adapted to allow a very large number of different types of proteins, protein variants or other biological molecules to be detected and quantified simultaneously on a single chip. Furthermore none of the prior art provides a suitable technology to directly build protein-specific electronic receptors on a chip without the use of any biological binding agents, synthetic probes or complex micro-structures such as test wells.

We disclose herein a novel, smaller, faster and more cost effective technique to detect, characterize and quantify individual proteins or other complex molecules on a chip. The technology described herein may also serve as a new method for DNA sequencing.

SUMMARY OF THE INVENTION

In one aspect the present invention provides a sensor which is capable of distinguishing between different molecular structures in a mixture. The device includes a substrate on which nanoscale binding sites in the form of multiple electrode clusters are fabricated. Each binding site includes nanometer scale points which extend above the surface of a substrate. These points are preferably nanoelectrodes which are spatially configured to provide a three-dimensional electro-chemical binding profile which mimics a chemical binding site. Thus, the binding sites have selective affinity for a complementary binding site on a target molecule or for the target molecule itself.

In one aspect, the binding sites are arranged in an array on the substrate. In one aspect, the spatial and electrochemical profiles of each site of the array are identical and provide an assay for a single target molecule. In another aspect, regions of the nanoelectrode array carry grouped arrays of electronically and/or spatially distinct binding sites for simultaneous detection and quantification of several molecular species.

In still another aspect, the materials used for the electrodes and surrounding surfaces are selected based on preferred intrinsic electrical and chemical properties.

The nanoelectrode array may be included in a chamber which can retain fluids. Several arrays may be used in a single chamber and several different chambers may be used on a single chip.

In still another aspect, the nanoelectrode array and chamber are attached to at least one micro-fluidic delivery and separation system such as a micro-capillary which allows both the delivery and separation by size and electrical properties of the proteins or other molecules to be analyzed.

In another aspect a microcontroller or microprocessor is provided to analyze signals from the nanoelectrodes and/or to time and control the fluidics separation of the molecules or proteins.

In another aspect the chip with the nanoelectrode arrays is associated with an electronic temperature control system such as a thermoelectric device having a thermistor to vary the bonding kinetics or the electrochemical affinity of the molecules with given nanoelectrodes, as well as the flow kinetics and separation of the molecules.

In another aspect the nanoelectrodes are interspaced in a linear microtube to sequence DNA.

Thus, it is an object of the present invention to provide a novel and rapid method to analyze small biological molecules in solution such as proteins and to sequence DNA by using semiconductor chip technology with extremely high packing densities.

It is a further object of the present invention to ensure that the entire chip can be easily integrated into devices for automated analysis of proteins, DNA or other molecules.

DETAILED DESCRIPTION OF THE PREFERRED EMBODIMENTS

The present invention is based in part on the fact that recent advances in technology such as the use of scanning tunneling microscopy (STM) has demonstrated that ultra small structures of a single or a few atomic layers can be built on a semiconductor surface such as silicon. Because of the size of these structures, they are generally referred to as nanostructures (one nanometer or $nm=10^{-9}m$, 1 Angstrom or $Å=10^{-10}$ m). These structures can be as small as a few Angstroms in diameter which is well below the Stokes radius of a small protein (which is approximately 25–35 Å). Since these structures can be built using different chemical elements (or the voltage applied to the structure can be selectively varied) and the spacial distribution, height width and shape of the structures can also be varied, these structures can be built in clusters to serve specifically as "molecular electrodes" whose electro-chemical properties and spacial distribution can be made to correspond precisely with the external three dimensional shape and electrochemical properties of molecules, preferably biochemicals and most preferably proteins. Therefore each of these clusters can serve as individual electronic protein "receptors" (or detectors). Since a very large number of these molecular electrodes can be placed on a single chip, the resulting arrays, termed here "nanoelectrode arrays" can be used to detect, characterize and quantify many different proteins on a single chip. In a variation of the technology, the chip can also be used to sequence DNA.

Figure 1:
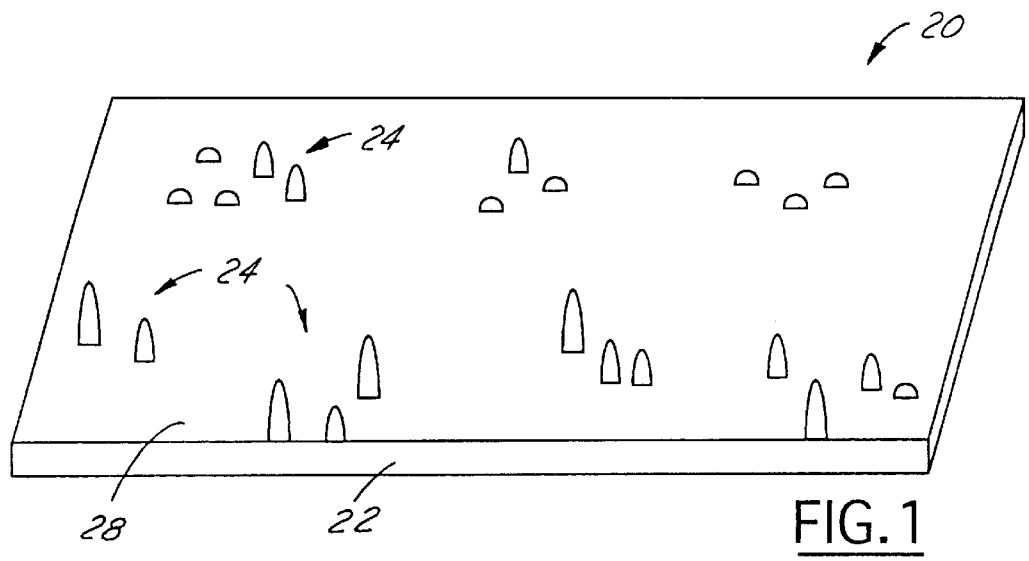
FIG. 1 is a perspective diagrammatic view of a nanoelectrode array showing different nanoelectrode clusters.
Figure 2:
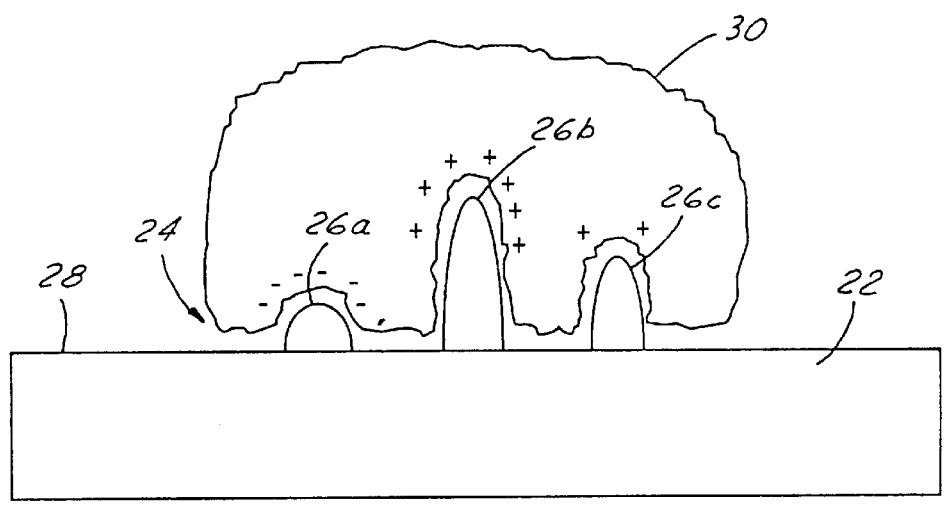
FIG. 2 is a side elevational diagrammatic view of a protein-specific electronic receptor and its matching protein.

Referring now to FIG. 1 of the drawings, microelectronic molecular sensor 20 is seen having substrate 22 on which an array of binding sites or clusters 24 are formed. Substrate 22 may comprise any number of materials such as silicon, germanium, gallium arsenide, or other semiconductors. Referring now to FIG. 2 of the drawings, one binding site 24 is shown in more detail having multiple electrodes 26a, 26b and 26c which are spatially distributed to form a pattern. Thus, it can be seen that each electrode 26a, 26b and 26c in this particular embodiment is spaced laterally from the adjacent electrode and is elevated at different heights off principal surface 28 of substrate 22.

It will be appreciated that through molecular modeling and empirical data, the topology of the binding sites and electrical charge are tailored to provide the required electrical and topographic properties to selectively recognize and bind a complementary region of a target molecule. As shown best in FIG. 2, protein 30 having a defined shape specific to that protein attaches to a given nanoelectrode cluster composed of three nanoelectrodes 26a, 26b and 26c. As will be explained more fully, each nanoelectrode may have slightly different electrochemical properties because of differing charges and/or chemical compositions. These individual electro-chemical properties match not only the electrochemical affinities of the amino acids or atoms present on the grooves of the protein but also complement the shape of the groove itself. Thus, when a molecule having the proper complementary profile binds to "receptor" 24 bridging the gap between the electrodes, a change in electrical potential occurs which can be monitored through appropriate circuitry to provide an indication of the presence of the target molecule.

In the most preferred embodiments of the present invention binding sites 24 have nanoscale geometries. As illustrated in FIG. 2, the distance from principal surface 28 to the top of electrode 26b is 1.9 nanometers, the width of electrode 26b is 0.7 nanometers and the distance between electrodes 26b and 26c is 1 nanometer. In general, each electrode will typically be between 0.2 and about 3 nanometers in height and from about 0.2 to about 2 nanometers in width. As used herein "nanoelectrode" shall include atomic scale as well as nanoscale structures, i.e. from 2 Å to 5 nanometers. That is, most preferably, each electrode (26a, 26b and 26c) extends from principal surface 28 a distance of from 2 Angstroms to 5 nanometers and have a width in this range. There will also typically be from about 2 to about 8 separate electrodes in each cluster 24. Electrodes 26a, 26b and 26c can be formed of a number of materials, either intrinsic or doped, such as gold and platinum and copper and other electrometals. Gold is particularly preferred. Also it may be suitable to form the electrodes of one material and coat the outer portion with a different material, e.g. gold coated with zinc oxide or gold coated with a thiol group.

Figure 2A:
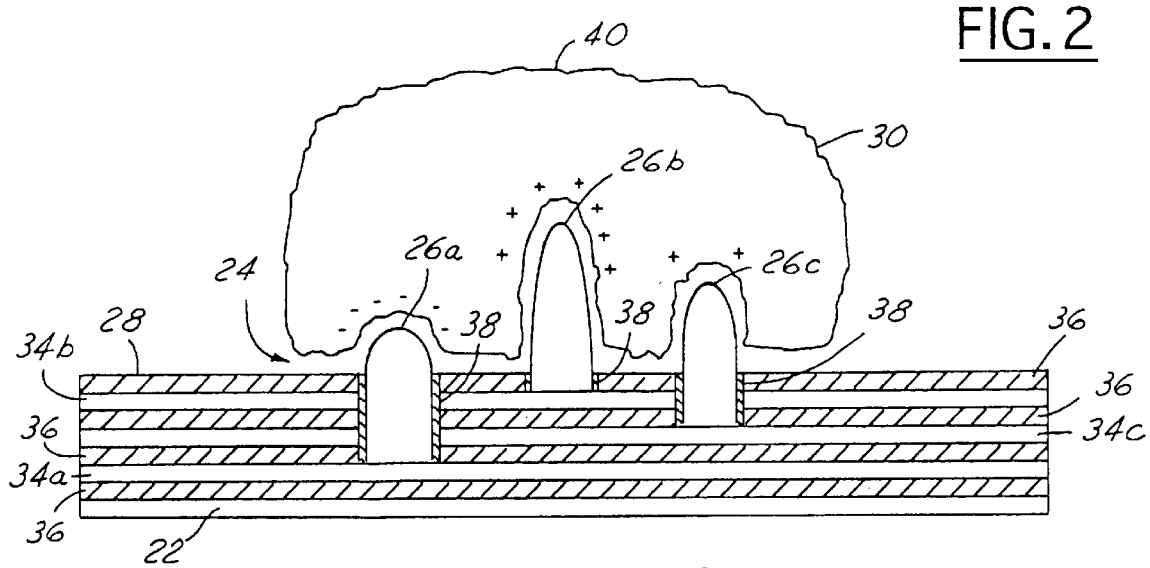
FIG. 2A is a side elevational cross-section of a protein-specific electronic receptor and its matching protein.

The electrodes may be each separately connected to a power source by small conductive regions or wires which may be formed of gold. In FIG. 2A, individual conductive layers 34a, 34b and 34c are shown electrically connecting their respective electrodes 26a, 26b and 26c. Dielectric layers 36 electrically isolate the individual conductive layers and dielectric sheaths 38 electrically isolate the individual electrodes. It will be appreciated that different potentials can be applied to the various individual electrodes and that electrodes from different clusters can be electrically linked to a single layer e.g., layer 34a. It will be appreciated that the various layers can be formed using conventional thin-film fabrication techniques such as CVD, thermal growth and ion implantation.

It has been shown recently that electrical "wires" can be built of single atoms (see for example review by Leo Kouwenhoven "Single-Molecule Transistors", Science Vol. 275, pages 1896–1897, 28 Mar. 1997, the entire disclosure of which is incorporated herein by reference). The wires can be deposited in a number of different ways as part of the microchip fabrication process, prior to the deposition of the nanoelectrodes. The nanoelectrodes can be deposited directly on the chip by Scanning Tunneling Microscope (as described in Kolb et al., Science pages 1097–1099, Vol. 275, Feb. 21, 1997, the entire disclosure of which is incorporated herein by reference). A number of other chip fabrication methods are possible such as different lithography techniques, etc.

In another aspect the nanoelectrodes are not connected to any electrical wires or conductive layers. In this case the binding of the protein or other molecule is simply dependent on the shape and chemical properties of the individual nanoelectrode clusters. Detection of the attachment of the given molecule to a given cluster can then be achieved by means other than electrical, for example by a highly precise x-y positional fluorescence reader, similar to that used for the DNA chip technology or by resonance.

In case the nanoelectrodes are not connected to wires (i.e. are not "live" electrodes), the nanoelectrodes may in some applications be interconnected in a given cluster. In this case the clusters would comprise interconnected peaks and grooves and these would form a larger structure (i.e. from 1 to >10 nanometers). This structure could be tailored either to match precisely the actual biological receptor of the target molecule or to allow the entire molecule to fit into a 3-dimensional "receptor" which would match at least a third of the overall 3-D shape of the molecule. In some instances and depending on the overall shape of the molecule, the receptor that is built may not necessarily include a site corresponding to the actual biological receptor of the target molecule.

Several types of binding or adsorption of the molecule to the nanoelectrode receptor are possible, depending on the chemical composition of the nanoelectrodes, the voltage and the chemical to be measured. Binding forces may include covalent binding, electrostatic binding, hydrogen bonds and van der Waals bonds.

Depending on the type of detection that is required, the individual nanoelectrodes of individual clusters do not necessarily need to be composed of different electrometals since both the spacial distribution and the height of the nanoelectrodes can be varied and these two variables may be enough for specific molecule detection in given applications. In some applications, each nanoelectrode can be selectively charged in a given cluster, allowing the electro-physical property of the nanoelectrode to be varied.

The entire sensor can be built using a computer controlled operation, where the spacing, height, width and the composition of the nanoelectrodes can be made to correspond exactly to the three dimensional shape and matching electrochemical properties of a selected molecule. Furthermore since the position of the nanoelectrode clusters corresponding to a given receptor for a given molecule is determined during the fabrication process, this position information can be used to detect attachment or binding. For example a large nanoelectrode array can be built with many different clusters, binding in a solution can be allowed, then the array be read using a highly accurate x-y reader in a way similar to the DNA chip. Computer control fabrication of the nanoelectrodes also allows for identical copies of the chip to be made.

It will be also be appreciated that the geometries that are built on the surface of the chip can be made to correspond exactly to the matching image of a crystallized protein surface taken from x-ray diffraction studies. Hence nanoelectrode array clusters can be built directly using crystallographic data and the resulting surfaces on the chip would favor protein-specific crystallization on given arrays.

In another aspect since multiple identical receptors can be built on the same chip, this technology can be used not only to detect given molecules but also to precisely estimate the quantity of these molecules present in the sample by measuring binding rates in identical clusters.

Figure 3:
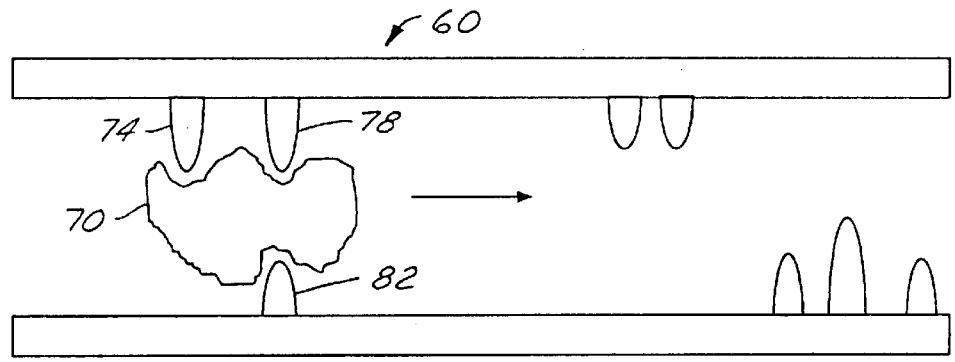
FIG. 3 is a side elevational cross-section of a nanoelectrode array inside a microfluidic tube, showing the trapping of a specific protein on its corresponding nanoelectrode receptor.

Referring to FIG. 3, two partial nanoelectrode arrays are shown facing each other and forming micro-channel or nanotube 60, which permits the flow of small molecules such as protein 70 therethrough. If protein 70 matches the shape of a receptor composed of electrodes 74, 78, and 82, the physical binding of the protein will cause a temporary minute change in the electrical signal which can be measured simultaneously in all said nanoelectrodes. The strength of the electrical signal can be modified for example by adding a conductant to the carrier solution for the molecules which need to be studied. Alternatively the nanoelectrodes themselves can be charged with a small current, which would change upon attachment of the given molecule.

Depending on the electrochemical properties of the nanoelectrodes and the analyte, the temperature and the flow rate, the binding may last only a fraction of a second or last longer. Time of retention in itself is another important variable which can be used in detecting and quantifying the types of molecules present in the sample.

In some applications, micro-channel 60 can form a part of a network of channels of different and specific sizes, matching the sizes of the proteins to measure. Each of these channels can be equipped with molecular sieves, allowing only proteins or molecules of certain size to pass through. The channels themselves can also serve as a means to separate molecules and deliver them to given detector chambers with nanoelectrode arrays which are specifically made to measure given classes of proteins or molecules of given molecular weights. In this case, each of the arrays would have nanoelectrodes with sizes corresponding to the sizes of the proteins to measure. As part of this network of channels, specific chambers can be added with specific functions such as a chamber to lyse cells. Other chambers can be filled with specific reagents which can be used as needed.

In another application each of the micro-channels is equipped with only one or a few nanoelectrode clusters and the protein mix is flowed through each of the channels. With the help of a microcontroller or a microprocessor controlling the flow rate in each micro-channel, the signals from each of the nanoelectrode clusters is then measured combining the power of the following variables for detection: protein separation rates (based on the size and charge of the proteins) and retention time on each given cluster (based on the shape and electrochemical properties of the molecule). Indeed the more a given molecule matches a given receptor, the longer it will bind. It is obvious that the sophisticated control and measure of the electrical signals in each nanoelectrode (as well as the control of all other variables such as sample flow rates, temperature, etc.) can only be done with the help of a microcontroller or a microprocessor.

Figure 4:
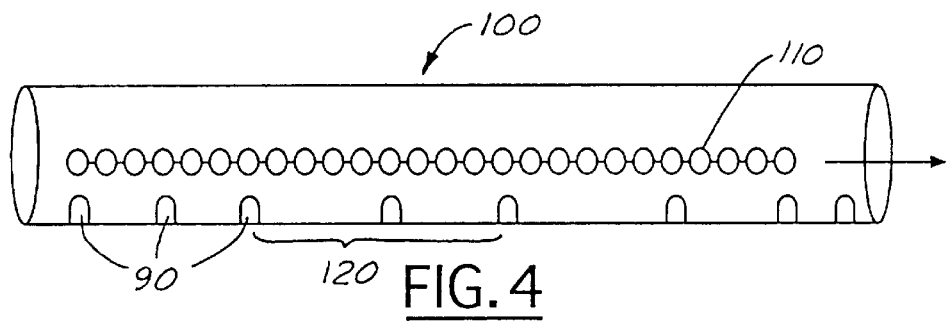
FIG. 4 is a diagrammatic side elevational cross-section of a microtube with a linear nanoelectrode array to detect DNA.

Referring now to FIG. 4, a nanoarray of electrodes 90 is built in a linear microtube 100 with the spacing and electrochemical composition of the nanoelectrodes varied in such a way to correspond exactly to the distance between given base pairs of a linear piece of DNA or RNA 110. In this case the nanoelectrodes are built using only two variables: precise spacing and electrochemical composition (not height) favoring position-specific binding of specific base pairs of DNA or RNA to matching nanoelectrodes. The principle that is applied here is that DNA is known to behave as a linear molecule when flowed in a microtube and that this rate of flow can be controlled and measured with precision. Furthermore the distance between 10 DNA base pairs being precisely 34 Å, the nanoelectrodes can be spaced precisely in multiples of 3.4 Å as shown in 120. By varying the spacing and charge and/or composition of the nanoelectrodes and by measuring the conductance changes over time in sequentially placed nanoelectrodes, an entire sequence is created, based on the timing of the signals of position-specific nanoelectrodes. The full DNA (or RNA) sequence is then reconstructed with the help of a microcontroller (or microprocessor) which can also control the flow rate in the microtube.

Analysis of Protein Variants

Mutations or other changes in the DNA result in aminoacid substitutions in the protein. These substitutions in turn result in conformational shape changes in the protein and can result in proteins that are either non-functional or have different properties. Since the three-dimensional (3-D) structure of proteins can now be inferred with precision on the basis of x-ray crystallography or nuclear magnetic resonance (NMR), the 3-D shapes of the protein variants can also be generated using the same method. Hence the entire spectrum of protein variants for given classes of proteins can be measured and quantified using the nanotechnology described above. This is because the conformational changes of each protein variant can be represented by a given nanoelectrode cluster varying in the shape, distribution and electro-chemical properties of the nanoelectrodes. In fact the building of the arrays can be computer-controlled and link the information matching the putative 3-D structure of proteins of interest (and their variants) to the micro fabrication of all the matching receptors on the chip. By measuring and quantifying these variants as described above, this approach represents a powerful alternative to direct DNA sequencing since all the possible mutation products of given genes which are expressed can be directly measured on a chip. Another advantage is that the chip would be fully reusable. Furthermore given the extremely high density of the nanoelectrode arrays that can be built on a single chip, the entire spectra of protein variants for many genes can be measured at once on the same chip. In fact with a refinement in the technology, all existing human proteins and their variants could theoretically be measured on a single chip of 1 $cm^2$ and the number of receptors that could be built on such a chip could theoretically exceed 1 billion which is a thousand fold improvement over any existing technology.

Protein Separation

As indicated above, the separation of molecules can be achieved by flowing said molecules in extremely small tubes (micro-capillaries, micro-channels or nanotubes) where smaller molecules travel faster than larger ones which are retained by friction and weak bonding interactions with the surfaces of the tubes. The result that is achieved is equivalent to electrophoresis but with the advantage of speed, cost and reusability of the micro-capillary.

Figure 5:
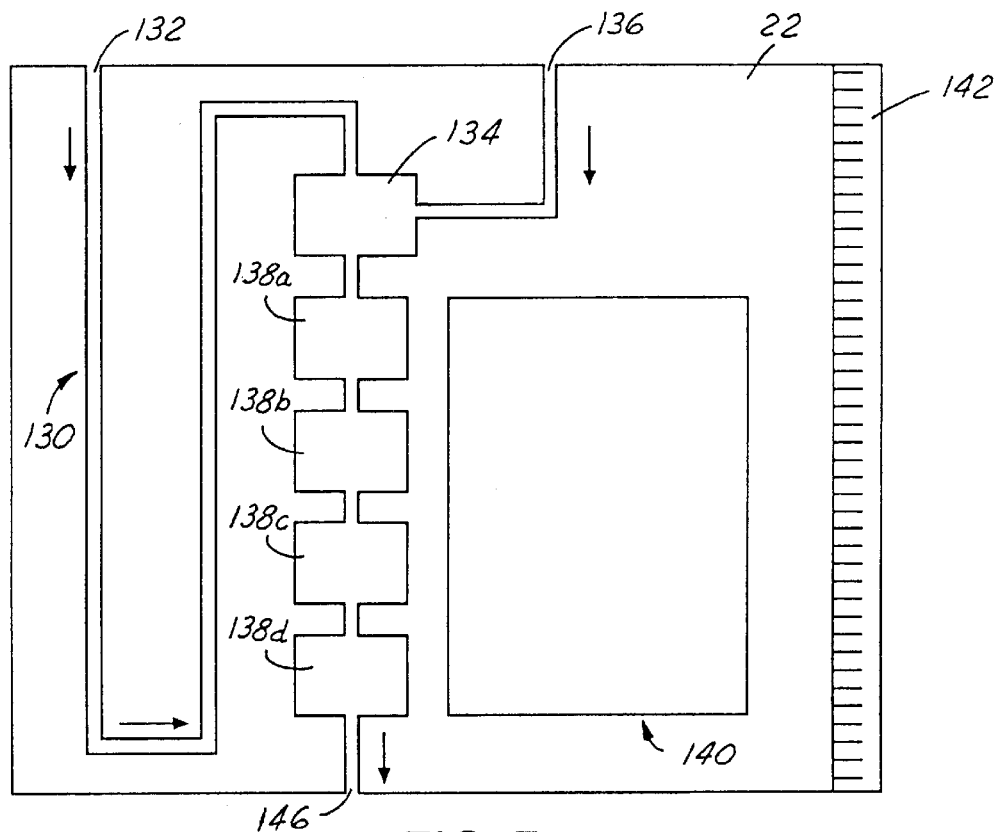
FIG. 5 is a cross-section of an integrated chip with nanoelectrode arrays, a micro-fluidic delivery system and associated electronics.

Referring now to FIG. 5, micro-channel 130 is shown with a sample input port 132 and a long loop flowing into an optional reagent micro-chamber 134, itself connected to an optional input port 136. Micro-channel 130 separates biological molecules by size and charge while micro-chamber 134 allows the selective input of an external reagent or solution. The flow and on/off position at each micro-channel juncture can be controlled electronically either by an external micro-pump (not shown), by thermocapillary action or by a change of electric potential. After entering micro-chamber 134, the analyte then flows successfully into micro-chambers 138a, 138b, 138c, then 138d, each holding different nanoelectrode arrays with nanoelectrode clusters of varying sizes and densities. In this particular design, the nanoelectrode arrays are fabricated immediately adjacent to a micro-electronics multiplexing or control area 140, itself connected to an interface 142. After reacting with successive nanoelectrode arrays in successive micro-chambers, the sample exits via port 146. The micro-channels and micro-chambers can either be etched in the silicon surface itself or can be fabricated separately on a surface of a material like glass, diamond, plastic or the like, which is then attached to the silicon surface.

This design can be varied in many different ways and FIG. 5 illustrates just one of many possible combinations of micro-channels, nanoelectrode arrays and micro-electronics that can be fabricated on a chip. As indicated above, a chamber allowing the lysing of the cells or viruses to be analyzed can also be included on the chip. Also it should be indicated that the directional flow in the micro-channels can be reversed and that each connecting micro-channel can be selectively opened or closed electrically. Hence when the test is completed the entire system can be heated to allow protein denaturation (and/or the potential in the nanoelectrodes can be reversed), then the system can be flushed with a solution to clean the nanoelectrode arrays and allow reuse of the chip.

Hence a complete and integrated protein separation and detection system can be built on a single chip. An important aspect of combining nanoelectrode arrays, micro-channels and a microcontroller (or a microprocessor) is that the time of separation (from sample injection into port 132 to time of first detection) and the length of retention on given nanoelectrode receptors are important variables for characterizing individual protein or protein variants. For example, the system can be calibrated by injecting known proteins, then known mixes of proteins, prior to injecting the sample to be tested. The time taken to reach a given nanoelectrode receptor and the length of binding on different electronic receptors would be specific to specific proteins (or to protein variants) and the signal-specific profiles for each protein can then be stored in memory and compared to those of the sample to be tested.

While FIG. 5 shows an integrated design, it is obvious that the protein separation component and the electronic components can also be placed externally and that the chip can be as simple as having a single nanoelectrode array enclosed in a single chamber with an interface. This chip (which may be disposable) can then be inserted into a larger module with the above components. Also, as indicated below, other detection methods can be used and the design of the chip would change accordingly.

Detection

Figure 6:
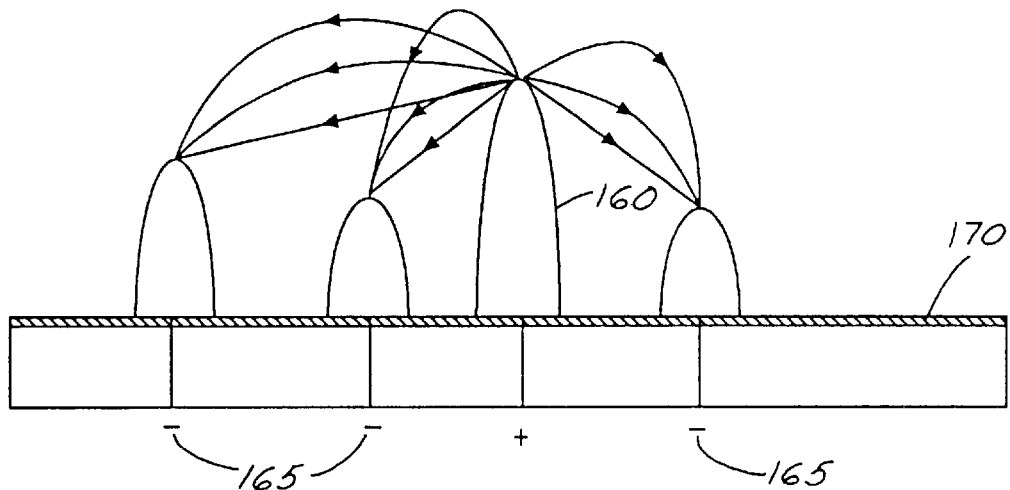
FIG. 6 is a side elevational cross-section of a nanoelectrode receptor showing the electrical field which is broken or modified upon binding of a specific molecule to said receptor.

There are many ways in which the binding or adsorption of the analyte on the nanoelectrode array can be detected. Referring now to FIG. 6, one way of detecting the signal due to adsorption on the nanoelectrode array is by electrical signal. In this case at least one of the electrodes in each cluster of a given array is used as a "source" 160 while the rest of the cluster 165 is used as a "sink." When an analyte, say a protein, is adsorbed it changes the flow of the current (pico ampere) as shown in FIG. 6. The electrodes are isolated by a layer of oxide 170. The unwanted effects of the electrical current can be avoided by using an AC approach.

Figure 7:
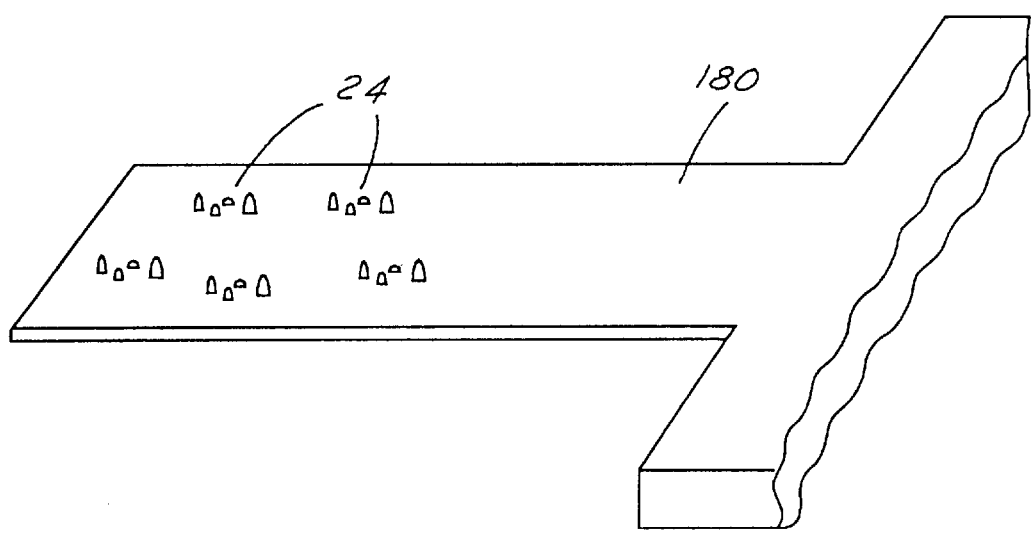
FIG. 7 is a view of a cantilevered nanoplate with several identical nanoelectrode clusters.

Referring now to FIG. 7, the second approach for detection of binding is by using a resonance approach. In this method, a nano structure is constructed. For example, nanoplate 180 of the dimension less than one micron is built. This structure can be free standing or it can be cantilevered. Identical sets of nanoelectrode receptors 24 are then fabricated on this surface. The structure is designed to have resonance frequency in the MHz to low GHz region. As the analyte flows past these structures, they spend a longer time on the cantilever if they have a structure that is complementary to the nanoelectrode structure. In other words, the analyte molecules undergo collision with the nanoplate. If there exists any complimentary nature between the analyte and the substrate, the analyte will spend more time on the surface during collision. This can be detected optically by shining a laser diode on the structure and detecting the reflected signal using a position sensitive photodiode. The AC signal in the photodiode shows the resonance response of the structure. The greater the signal, the larger the concentration of bound biological molecules, i.e. the greater the concentration of the said molecule in the solution. Other detection techniques such as capacitive, piezoresistive, piezoelectric, electron tunneling, etc. could also be used.

The structure can be excited into resonance response by mechanical means using a piezoelectric element. In this technique, a nanoplate structure is attached to a piezoelectric material which can be vibrated using an AC signal. At resonance the structures oscillate with maximum amplitude. It can also be excited into resonance by modulating the diode laser using square wave power pulses. Since square waves contain all the Fourier components, there will be a component that corresponds to the resonance frequency of the structure.

Since these nanoelectrodes can be constructed on geometrical structures with extremely small thermal mass (for example, nanoplates have a thermal mass of the order of many picograms or less), they can be heated and cooled in the micro to milliseconds time frame. This fact can be used to adsorb and desorb analytes in a periodic fashion. However, when there is a complimentary structure between surface and the analytes the desorption time scale will be different.

Use of an External Detector

In another detection application the entire chip which has been allowed to react with the sample is placed in a x-y laser reader in a manner similar to the DNA chip. In this case the chip is incorporated into a highly precise holder to ensure accurate position reading of each cluster. Detection may be done by fluorescence, for example after reaction of the bound samples to the clusters with a fluorescent molecule or with labeled antibodies.

Detection may also be done by other means such as laser-desorption-ionization mass spectrometry.

Nanoelectrode Construction

Nanoelectrode arrays can be constructed on a doped semiconductor substrate by nanolithography using scanning probes. In this approach, metal clusters are deposited either from a solution or by field evaporation from a STM/AFM tip. Since the electric field between the tip and the substrate is very high ($10^9$ V/m), many metals can be field evaporated. In solution many metals can be electrochemically deposited on a surface. The surface of the semiconductor can be oxidized to be an insulator.

Nanometer scale trenches and lines can be made on a semiconductor surface using STM tip in an oxide etching solution producing a trench. The depth of the trench depends on the time spent by the tip at that location and the voltage on the tip. Hence not only can the nanoelectrodes be built by deposition but they can also be built by etching. The trenches can also be used to make the channels to separate the proteins, as instructed above.

It should also be noted that nanotransistors can be built directly in the chip to facilitate detection and increase the density of the detectors. The nanotransistors can be build prior to the deposition of the nanoelectrodes as a sub-layer in the overall chip manufacturing process or be placed on an adjacent part of the chip.

The above-described principles illustrate the wide variety of applications that are possible in the micro fabrication and applications of the nanoelectrode arrays. For example the entire system from sample input to detection with output signals sent to an external device such as a monitor can be built on a single chip, using micro-channels (for sample separation and delivery), miniature ionic pumps, sample detection, a built-in microcontroller, a method for temperature control, etc. This chip can be inserted into a measuring device, for example for use in a physician's office or into a field detector. If a very large nanosensor array is used, it may be preferable to use a microprocessor or several microcontrollers to control the above described functions. In some applications the large arrays can be used with an external laser reader. In this case the array can be used in a way similar to the DNA chip, where the entire chip is allowed to react with the entire sample, washed and then inserted into an external reader. Using this approach the chip can be build into a convenient handling cassette.

While the invention has been described with respect to specific embodiment for complete and clear disclosure, the appended claims are not to be thus limited but are to be construed as embodying all modifications and alternative constructions that may occur to one skilled in the art which fairly fall within the basic teaching here set forth.

What is claimed is:

1. A sensor for detecting biological molecules, said sensor comprising:

a substrate;

an electrode on said substrate, said electrode having the capacity to bind a preselected biological molecule, said electrode extending from a principal surface of said substrate a distance of from 2 Angstroms to 5 nanometers and said electrode having a width of from 2 Angstroms to 5 nanometers.

2. The sensor recited in claim 1, wherein said substrate has a plurality of said electrodes.

3. The sensor recited in claim 2, wherein each of said electrodes has an identical chemical composition.

4. The sensor recited in claim 2, wherein at least one of said electrodes has a chemical composition which is different than another of said electrodes.

5. The sensor recited in claim 1, wherein said electrode has an outer coating.

6. The sensor recited in claim 2, wherein each of said electrodes has a chemical coating.

7. The sensor recited in claim 6, wherein each of said coatings has the same chemical composition.

8. The sensor recited in claim 6, wherein at least one of said coatings is different than another of said coatings.

9. The sensor recited in claim 2, wherein the plurality of said electrodes extend from a principal surface of said substrate and wherein at least one of said electrodes extends farther from said principal surface than another of said electrodes.

10. The sensor recited in claim 2, wherein the width of at least one of said electrode is greater than the width of another of said electrodes.

11. The sensor recited in claim 2, wherein said electrodes are spaced laterally from one another on said substrate.

12. The sensor recited in claim 2, wherein said electrodes are arranged in clusters on said substrate.

13. The sensor recited in claim 12, wherein said clusters are spaced to form an array.

14. The sensor recited in claim 2, wherein the electrochemical properties, width and spacing of said electrodes complement and bind a site on said biological molecules.

15. The sensor recited in claim 2, wherein said electrodes are connected to nanowires.

16. The sensor recited in claim 2, further comprising a support structure for said substrate, said support structure being adapted to be received in a x-y fluorescent laser reader.

17. The sensor recited in claim 1, wherein said electrode is connected to at least one electrically conductive nanowire.

18. The sensor recited in claim 1, further comprising an interface connecting said sensor to a control system.

19. The sensor recited in claim 1, wherein said biological molecules are proteins.

20. A sensor for detecting proteins, said sensor comprising:

a micro-capillary tube;

a plurality of electrodes disposed in said tube, said electrodes having the capacity to bind a preselected protein, said electrodes being between about $10^{-9}$ and $10^{-10}$ meters in height and width.

21. The sensor recited in claim 20, further comprising a microcontroller.

22. The sensor recited in claim 21, further comprising a system to regulate the temperature of said sensor.

23. A method of sequencing nucleic acids, comprising the steps of:

providing a sensor assembly, said sensor assembly having a substrate on which plurality of electrodes are disposed, said electrodes each extending from a principal surface of said substrate a distance of from 2 Angstroms to 5 nanometers and having a width of from 2 Angstroms to 5 nanometers;

contacting said electrodes with a solution containing nucleic acids;

said electrodes having the capacity to bind at least some of said nucleic acids.

24. The method recited in claim 23, wherein said nucleic acids are DNA and wherein said electrodes are spaced apart from one another to complement and bind to DNA base pairs of a linear DNA molecule.

25. The method recited in claim 23, wherein said sensor assembly includes a microtube in which said electrodes are disposed.

26. The method recited in claim 25, wherein said sensor assembly further comprises a flow control system and a laser detector.

27. The method recited in claim 23, wherein said sensor assembly further comprises a microcontroller and a display.

28. The method recited in claim 23, wherein said nucleic acids are RNA.

* * * * *

UNITED STATES PATENT AND TRADEMARK OFFICE
CERTIFICATE OF CORRECTION

PATENT NO. : 6,123,819
DATED : SEPTEMBER 26, 2000
INVENTOR(S) : PEETERS

It is certified that error appears in the above-identified patent and that said Letters Patent are hereby corrected as shown below:

Claim 10, column 11, line 44, delete "electrode" and insert --electrodes--

Signed and Sealed this

First Day of May, 2001

Attest:

NICHOLAS P. GODICI

*Attesting Officer*   *Acting Director of the United States Patent and Trademark Office*